United States Patent
Insley et al.

(10) Patent No.: US 7,892,347 B2
(45) Date of Patent: *Feb. 22, 2011

(54) INJECTABLE CALCIUM PHOSPHATE CEMENT

(75) Inventors: Gerard M. Insley, Limerick (IE); Adrian Sun Wai, Limerick (IE); Donal O'Mahony, Limerick (IE); Paul Higham, Ringwood, NJ (US); Joseph P. Zitelli, River Edge, NJ (US); Sandra M. Murray, Oradell, NJ (US); Brian Hess, Charlestown, MA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/640,805

(22) Filed: Dec. 17, 2009

(65) Prior Publication Data

US 2010/0095870 A1 Apr. 22, 2010

Related U.S. Application Data

(60) Division of application No. 12/290,225, filed on Oct. 28, 2008, which is a continuation of application No. 11/312,094, filed on Dec. 20, 2005, now Pat. No. 7,459,018, which is a continuation-in-part of application No. 11/102,254, filed on Apr. 8, 2005, now Pat. No. 7,416,602.

(51) Int. Cl.
C04B 12/02 (2006.01)
(52) U.S. Cl. .................. 106/690; 106/691; 106/35
(58) Field of Classification Search .............. 623/23.63; 106/690, 691, 35
See application file for complete search history.

(56) References Cited

U.S. PATENT DOCUMENTS

| | | |
|---|---|---|
| 2,018,410 A | 10/1935 | McDonald |
| 4,139,599 A | 2/1979 | Tomlinson et al. |
| 4,244,931 A | 1/1981 | Jarvis et al. |
| 4,312,843 A | 1/1982 | Monty et al. |
| 4,472,365 A | 9/1984 | Michel |
| 4,612,053 A | 9/1986 | Brown et al. |
| 4,828,823 A | 5/1989 | Li |

(Continued)

FOREIGN PATENT DOCUMENTS

EP 0 627 899 12/1994

(Continued)

OTHER PUBLICATIONS

Gbureck, Dembski, Thull, Barralet, "Factors influencing calcium phosphate cement shelf-life", Biomaterials, May 26, 2004.

(Continued)

*Primary Examiner*—Paul Marcantoni
(74) *Attorney, Agent, or Firm*—Lerner, David, Littenberg, Krumholz & Mentlik, LLP

(57) ABSTRACT

The invention is related to a premixed putty calcium phosphate composition comprising at least two calcium phosphate minerals, at least one reaction retarding agent, at least one binding agent, at least one sodium phosphate, and at least one nonaqueous extender, wherein one of said at least two calcium phosphate minerals contains a stabilizing agent.

6 Claims, 4 Drawing Sheets

U.S. PATENT DOCUMENTS

| | | | |
|---|---|---|---|
| 4,880,610 | A | 11/1989 | Constantz |
| RE33,161 | E | 2/1990 | Brown et al. |
| RE33,221 | E | 5/1990 | Brown et al. |
| 4,973,168 | A | 11/1990 | Chan et al. |
| 5,024,825 | A | 6/1991 | Buhl et al. |
| 5,047,031 | A | 9/1991 | Constantz |
| 5,129,905 | A | 7/1992 | Constantz |
| 5,149,368 | A | 9/1992 | Liu et al. |
| 5,178,845 | A | 1/1993 | Constantz et al. |
| 5,262,166 | A | 11/1993 | Liu et al. |
| 5,336,264 | A | 8/1994 | Constanz et al. |
| 5,342,441 | A | 8/1994 | Mandai et al. |
| 5,427,756 | A | 6/1995 | Dany et al. |
| 5,522,893 | A | 6/1996 | Chow et al. |
| 5,525,148 | A | 6/1996 | Chow |
| 5,542,973 | A | 8/1996 | Chow et al. |
| 5,545,254 | A | 8/1996 | Chow |
| 5,569,442 | A | 10/1996 | Fulmer et al. |
| 5,605,713 | A | 2/1997 | Boltong |
| 5,697,981 | A | 12/1997 | Ison et al. |
| 5,709,742 | A | 1/1998 | Fulmer et al. |
| 5,782,971 | A | 7/1998 | Constantz et al. |
| 5,820,632 | A | 10/1998 | Constantz et al. |
| 5,900,254 | A | 5/1999 | Constantz |
| 5,952,010 | A | 9/1999 | Constantz |
| 5,962,028 | A | 10/1999 | Constantz |
| 5,968,253 | A | 10/1999 | Poser et al. |
| 6,002,065 | A | 12/1999 | Constantz et al. |
| 6,005,162 | A | 12/1999 | Constantz |
| 6,117,456 | A | 9/2000 | Lee et al. |
| 6,206,957 | B1 | 3/2001 | Driessens et al. |
| 6,375,935 | B1 | 4/2002 | Constantz |
| 6,379,453 | B1 | 4/2002 | Lin et al. |
| 6,409,972 | B1 | 6/2002 | Chan |
| 6,642,285 | B1 | 11/2003 | Bohner |
| 6,719,993 | B2 | 4/2004 | Constantz |
| 6,733,582 | B1 | 5/2004 | Bohner et al. |
| 6,793,725 | B2 | 9/2004 | Chow et al. |
| 6,929,692 | B2 | 8/2005 | Tas |
| 7,416,602 | B2 * | 8/2008 | Murphy et al. ............ 106/690 |
| 7,459,018 | B2 * | 12/2008 | Insley et al. ............... 106/690 |
| 2002/0055143 | A1 | 5/2002 | Bell et al. |
| 2002/0155167 | A1 | 10/2002 | Lee et al. |
| 2003/0021824 | A1 | 1/2003 | Lacout et al. |
| 2003/0049329 | A1 | 3/2003 | Lee et al. |
| 2004/0244651 | A1 | 12/2004 | Lemaitre et al. |
| 2005/0074415 | A1 | 4/2005 | Chow et al. |
| 2005/0199156 | A1 | 9/2005 | Khairoun et al. |
| 2009/0158964 | A1 * | 6/2009 | Insley et al. ............... 106/691 |

FOREIGN PATENT DOCUMENTS

| | | |
|---|---|---|
| EP | 0 936 929 | 8/1999 |
| EP | 1 237 585 | 9/2002 |
| EP | 0 912 161 B1 | 2/2003 |
| EP | 1 443 981 | 8/2004 |
| WO | 93/16657 | 9/1993 |
| WO | 98/16268 A2 | 4/1998 |
| WO | 00/07639 A1 | 2/2000 |
| WO | 01/41824 A1 | 6/2001 |
| WO | 2004/000374 A1 | 12/2003 |
| WO | 2004/103419 | 12/2004 |
| WO | 2005/009481 | 2/2005 |
| WO | 2005/084726 | 9/2005 |

OTHER PUBLICATIONS

Freche, M. & Heughebaert, J.C.; Calcium Phosphate Precipitation in the 60-80oC Range, Journal of Crsytal Growth, vol. 94 (1989), pp. 947-954.

Komath, Varma and Sivakumar, "On the development of an apatitic calcium phosphate bone cement", Bull. Matter. Sci, vol. 23, No. 2, Apr. 2000, pp. 135-140.

Burguera, Guitian, Chow, "A water setting tetracalcium phosphate-dicalcium phosphate dihydrate cement", Wiley Periodicals, vol. 71A, No. 2, Oct. 2004.

Murphy, Clarkin & Insley,'Calcium Phosphate Bone Cements of the Future: Towards the Understanding of their Chemistry', Biomaterials Research Group, Sep. 2005.

Chow et al., IADR Abstract No. 2410, Apr. 1991.

Chow et al., AADR Abstract, No. 666, 1992.

Biotek, Inc.,"Hydroformed Microspheres as New Injectable Drug Vehicle", 1994.

Gisep, Kugler, Wahl, Rahn, 'Mechanical Characterization of a Bone Defect Model Filled with Ceramic Cements', J Mater Sci Mater Med, vol. 15, No. 10, pp. 1065-1071, Oct. 2004.

Jensen, Ooms, Verdonschot, Wolke, 'Injectable Calcium Phosphate Cement For Bone Repair and Implant Fixation', Orthop Clin North Am, vol. 36, No. 1, pp. 89-95, Jan. 2005.

Burguera EF, Xu HH, Weir MD, Injectable and rapid-setting calcium phosphate bone cement with dicalcium phosphate dihydrate, J Biomed Mater res B Appl Biomater, Sep. 23, 2005.

Tofighi A, Mounic S, Chakaravarthy P, Rey C, Lee D, "Setting Reactions Involved in Injectable Cements Based on Amorphous Calcium Phosphate", Key Engineering Materials, vol. 192-195, pp. 769-772, 2001.

Barralet, Grover, Gbureck, 'Ionic Modification of Calcium Phosphate Cement Viscosity. Part II: Hypodermic Injection and Strength Improvement of Brushite Cement.', Biomaterials, vol. 25, No. 11, pp. 2197-2203, May 2004.

Gbureck, Barralet, Spatz, Grover, Thull 'Ionic Modification of Calcium Phosphate Cement Viscosity. Part I: Hypodermic Injection and Strength Improvement of Apatite Cement.', Biomaterials, vol. 25, No. 11, pp. 2187-2195, May 2004.

Komath, Varma , "Development of a fully injectable calcium phosphate cement for Orthopedic and Dental Applications", Bull. Matter. Sci, Jun. 2003, pp. 415-422.

* cited by examiner

INJECTABLE CALCIUM PHOSPHATE CEMENT

CROSS-REFERENCE TO RELATED APPLICATIONS

This application is a divisional of U.S. application Ser. No. 12/290,225, filed on Oct. 28, 2008, which is a continuation of U.S. patent application Ser. No. 11/312,094, filed Dec. 20, 2005, which is a continuation-in-part of U.S. application Ser. No. 11/102,254, filed on Apr. 8, 2005, the disclosure of which is incorporated herein by reference.

BACKGROUND OF THE INVENTION

The field of this invention pertains to calcium phosphate minerals for bone cement or bone filler applications and in the preparation of such cement. More specifically, this invention relates to a calcium phosphate bone cement comprising a mixture of tetra-calcium phosphate and di-calcium phosphate in an aqueous solution, in which the mixture then sets to form a bone cement with a substantial portion of the cement being hydroxyapatite.

Hydroxyapatite is the major natural building block of bone and teeth. It has been found that bone cements, which are formed by combining calcium and phosphate precursors in an aqueous solution, which initially forms a paste but then hardens into a hydroxyapatite bone cement, are useful in fixing fractures and bone defects. Hydroxyapatite has a calcium to phosphorous ratio of approximately 1.67 which is generally the same as the calcium phosphate ratio in natural bone structures.

These pastes may be placed in situ prior to setting in situations where bone has been broken, destroyed, degraded, become too brittle or has been the subject of other deteriorating effects. Numerous calcium phosphate bone cements have been proposed such as those taught by Brown and Chow in U.S. Reissue Pat. Nos. 33,161 and 33,221, Chow and Takagi in U.S. Pat. No. 5,522,893, and by Constantz in U.S. Pat. Nos. 4,880,610 and 5,047,031.

It has been well known since the initial use of calcium phosphate cements that the addition of sodium phosphate solutions, potassium phosphate solutions or sodium carbonate solutions to the aqueous setting solution of the calcium phosphate precursors can speed setting times. This is documented in the Chow et al., April, 1991 IADR Abstract No.: 2410 and AADR, 1992 Abstract No.: 666 and was known to those skilled in the art prior to these publications.

Typically, the powder components, which may be a combination of tetra-calcium phosphate and di-calcium phosphate is supplied in a sterile form in a blister pack or a bottle, e.g., with contents of 2 to 50 g. The liquid, e.g. a molar sodium phosphate solution, distilled water or sodium chloride solution is usually present in a sterile, glass container, usually a disposable syringe, having a volume of 10 cc. The powder and liquid components are usually mixed in a vessel, and processed from this vessel, e.g., by means of a syringe or the like.

It is important that these components of bone cements have long-term stability during storage as these components may be stored for weeks or months before usage when the powder component is mixed with the aqueous component to form a settable material. But, the long-term stability of these components have not been extensively studied because it has been assumed by those skilled in the art that they stay stable with little or no change in properties.

However, unlike the industry's general assumption, according to Uwe Gbureck et al. in *Factors Influencing Calcium Phosphate Cement Shelf-life*, Biomaterials, (Elsevier Ltd. 2004), it has been found that some prior art powder mixtures of calcium phosphate lose their ability to set after only 7 days of storage, despite being stored in sealed containers. The deterioration of the prior art powder mixtures was subsequently found to be related to their conversion to monetite in a dry state during aging.

Thus, there is a need to develop a rapid setting bone cement which overcomes the destabilization problems of the prior art.

Furthermore, there is also a need to develop an injectable and rapid setting bone cement which can be used in a minimally invasive manner. Minimally invasive surgery is often performed through natural body openings or small "keyhole" incisions, sometimes no more than a quarter-inch in length. When working through such a small opening, it is often desired or required to use a bone cement which can be injected by means of a syringe, for example, into the fractured area.

The commercially available injectable cements currently available in the market, such as Synthes Norian SRS®, Synthes Norian CRS® and Wright Medical MIG X3®, are formulated so that they are readily injectable. However, they have longer setting times, forcing the surgeon to wait as the cements set, prolonging the surgery time.

Some other commercially available bone cement products, such as Synthes Fast Set Putty®, Lorenz Mimix® are rapid setting, but are not readily injectable through a syringe or a needle, rendering the product useless for minimally invasive applications.

Therefore, there is also a continued need to develop a rapid setting bone cement with long-term stability, and also is readily injectable, providing a surgeon with optimal working time and a decreased overall set-time during a minimally invasive surgery.

The invention that is described herein fulfills all of the shortcomings of the currently available commercial products described above.

SUMMARY OF TEE INVENTION

It is one aspect of the present invention to provide a rapid setting injectable calcium phosphate bone cement, preferably with long term shelf-life.

It is also an aspect of the present invention to provide a calcium phosphate bone cement that provides an optimal combination of injectability and rapid-setting to meet a surgeon's needs. For example, in some embodiments, the cement of the present invention can be easily molded in vivo (intraoperatively).

It is further an aspect of the present invention to provide a fully injectable bone cement product without the liquid and powder separation when mixed.

It is another aspect of the present invention to provide a calcium phosphate bone cement with significantly improved mechanical strength properties. For example, soon after the bone cement minerals of the present invention are mixed and applied to the defect area, one can drill and put screws into the cement without cracking, which is a common challenge with the commercially available products today.

Furthermore, it is an aspect of the invention to provide a method for making a calcium phosphate bone cement described above and supplying the same as a kit. For example, in one aspect of the invention, a kit for forming a calcium phosphate bone cement comprises: (a) a first container comprising a powder mixture of stabilized di-calcium phosphate dihydrate containing from about 10 ppm to about 60 ppm of magnesium, a second calcium phosphate mineral, and at least one reaction retarding agent, and (b) a second container comprising a solvent comprising at least one binding agent, and at least one sodium phosphate compound.

In one aspect of the invention, a calcium phosphate cement comprises (1) at least one source of calcium phosphate, (2) at least one reaction retarding agent, (3) at least one binding agent, and (4) at least one sodium phosphate compound. It will be appreciated that when the components are mixed and/or set, it may or may not be possible to identify or distinguish these individual components. Thus, references to "cement" herein include a cement which results from the mixture and/or reaction of these components.

In another aspect of the invention, a calcium phosphate bone cement comprises the product of a mixture of a powder component and a liquid component, wherein at least one source of calcium phosphate is a part the powder component, and at least one reaction retarding agent, at least one binding agent, and at least one sodium phosphate compound are a part of either the powder component or the liquid component.

In yet another aspect of the invention, an injectable calcium phosphate cement comprises a powder component comprising (1) a di-calcium phosphate mineral containing from about 10 ppm to about 60 ppm of a stabilizing agent, (2) a tetracalcium phoshpate mineral, (3) and a reaction retarding agent; and a liquid component comprising (1) at least one binding agent, (2) at least one sodium phosphate, and (3) solvent.

BRIEF DESCRIPTION OF TEE DRAWINGS

DETAILED DESCRIPTION

Figure 1:
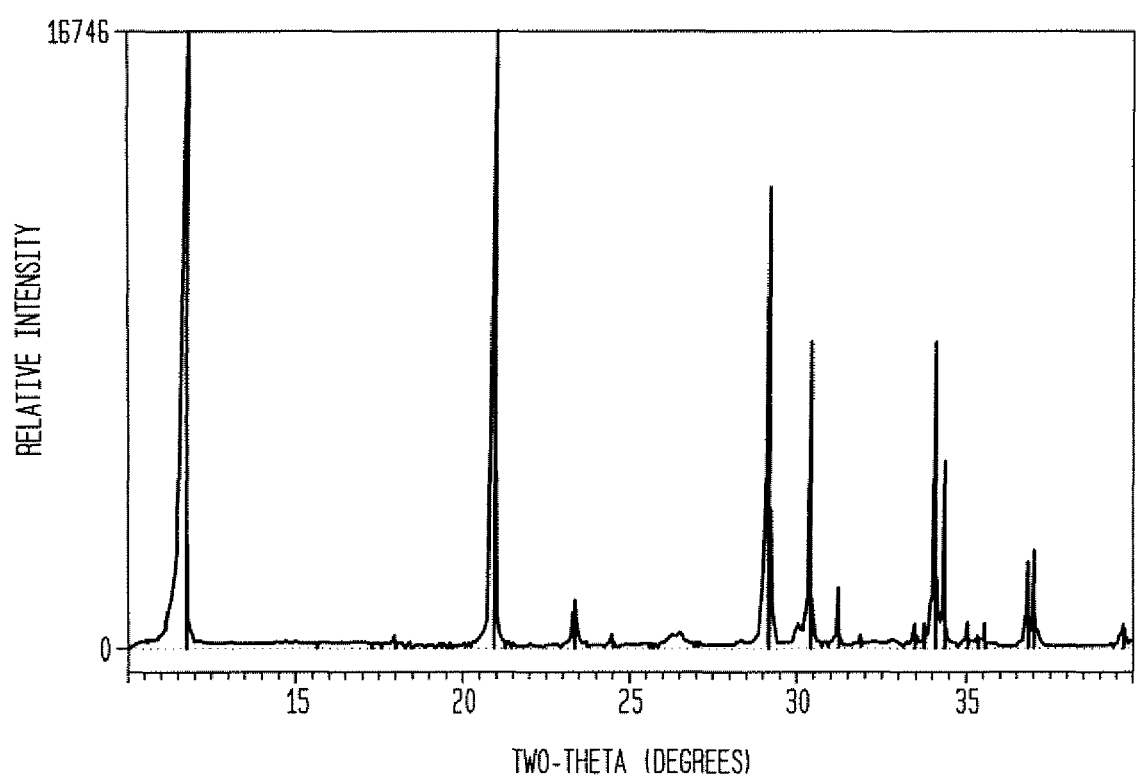
FIG. 1 is a characteristic X-ray powder diffraction pattern of DCPD containing 40 ppm of magnesium before the accelerated aging test.

Throughout the entire specification, including the claims, the word "comprise" and variations of the word, such as "comprising" and "comprises," as well as "have," having," "includes," "include," and "including," and variations thereof, means that the named steps, elements or materials to which it refers are essential, but other steps, elements, or materials may be added and still form a construct with the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps. The term "cement" herein is used interchangeably with paste, slurry, putty, cement formulation and cement composition. The term "between" as used in connection with a range includes the endpoints unless the context suggests otherwise. The term "long term shelf-life" herein means that the calcium phosphate mineral(s) will set when mixed with a solvent to form a cement after the powder has been stored in a sealed container either with or without the other powder components such as reaction retarding agent for a predetermined period of time, preferably for at least 1.5 months, more preferably 3 months, and most preferably for at least 6 months or more according to the accelerated aging test described in details below in Example 9. The term "injectable" as used in accordance with the present invention herein means that when the calcium phosphate mineral(s) are mixed with a solvent to form a cement paste and the paste is transferred to a syringe fitted with a 10 gauge cannula, the injection force measured after 4 minutes and 30 seconds from the initial blending of the mixture at the ambient temperature of between 18° C. to 22° C. as set out in Example 12 below, does not exceed 200 N, and more preferably 150 N. The term "rapid setting" as used in accordance with the present invention herein means that the calcium phosphate mineral(s) will set when mixed with a solvent to form a cement in about 10 minutes, preferably in about 9 minutes, most preferably in about 8 minutes, when applied to a defect area, wherein the defect temperature is about 32° C. The term "set" as used in accordance with the present invention herein means that the penetration force measured according to the wet field penetration resistance test described in details below in Example 10 is greater than 3500 pst (24.1 MPa).

Reaction Retarding Agent

The reaction retarding agent in accordance with the present invention can be any material useful for retarding the formation of hydroxyapatite when calcium phosphate minerals are mixed with a solvent to form hydroxyapatite. If the calcium phosphate minerals set too fast, then it results in inhomogeneous porous cement matrix, which results in low compressive strength. Therefore, a reaction retarding agent is used to slow the rapid dissolution of calcium phosphate minerals during cement mixing and injection.

The reaction retarding agent of the present invention may be supplied to an end user as a powder component or dissolved in a liquid component with a solvent. However, in a preferred embodiment, the reaction retarding agent is a powder component.

Examples of a reaction retarding agent which can be used in the present invention, without limitation, are trisodium citrate, tripotassium citrate, sodium pyrophosphate, EDTA (ethylene diamine tetra acetic acid sodium salt), citric acid, and/or a mixture thereof. The preferred reaction retarding agent is trisodium citrate.

Furthermore, the particle size and/or amount of the reaction retarding agent can be adjusted to modify the rate of the rapid dissolution of calcium phosphate minerals during cement mixing and injection. For example, the amount and/or particle size of the reaction retarding agent can be varied so that the bone cement composition is formulated to be delivered to a fractured area in a long delivery system before it sets.

The particle size of the reaction retarding agent (as well as all other powder components) was measured using Beckman Coulter's LS 13320 Series particle size analyzer. A sample for analysis was prepared by adding 0.03 gram of powder and 2.5 mL of a carrier medium (in this case, ethanol was used) to a beaker. The slurry was mixed aggressively for 15 seconds and then was transferred to a small volume module of the Coulter counter. Prior to the analysis of the sample, a background count was achieved by first, cleaning the small volume module two times with ethanol and then filling the cell with ethanol. The stirrer speed was turned on to 50% and the measurement of the background was taken. If necessary, the cell can be further cleaned using ethanol.

For sample analysis, the slurry of a reaction retarding agent and ethanol mixture was added to the cell until an obscuration value of roughly 10% was obtained. This sampling procedure was performed with the cell stirring set at 50% to avoid settling of the suspension during sampling.

Volume distributions were then obtained. Upon measurement completion, the cell was emptied and cleaned and refilled with the slurry of reaction retarding agent and ethanol mixture, and the sample procedure repeated for a total of three times.

It is noted that the particle size values mentioned herein refer to Volume Mean Diameter values. Particle size distribution can be measured by Becton Coulter's LS 13 3220 series particle size analyzer as known to those skilled in the art and as further disclosed and discussed above.

In accordance with the present invention, the particle size of the reaction retarding agent is between about 1 μm to about 1000 μm, preferably between about 170 μm to about 220 μm. This means that at least about 25%, preferably about 50%, more preferably about 75% of the reaction retarding agent, by weight, falls within these ranges based on sieving.

In accordance with the present invention the reaction retarding agent can be provided as a powder component, or dissolved in a solvent and provided as a liquid component.

With respect to the amount of the reaction retarding agent, the reaction retarding agent may be present in an amount of between about 3% and about 20%, more preferably between about 5% and about 10% based on the total weight of the formulation.

In a preferred embodiment of the present invention, the reaction retarding agent of the present invention is supplied to an end user as a part of the powder component, wherein the reaction retarding agent may be present in an amount of between about 3% and about 15%, more preferably between about 5% and about 12.5% based on the total weight of the powder component.

Binding Agent

The binding agent of the present invention is used to impart cohesive qualities to the powder material and to improve the free-flowing qualities. The binding agent also aids the mixed cement to flow through the syringe and/or cannula easily. The binding agent binds the components together, providing a fully injectable bone cement product without the liquid and powder separation, which is a common challenge with the commercially available products today.

The binding agent of the present invention may be supplied to an end user as a powder component or dissolved in a liquid component with a solvent. However, in a preferred embodiment, the binding agent is dissolved in a solvent and provides as a liquid component.

It is preferred that the binding agent is provided as a part of the liquid component since some of the binding agents may be cleaved or cross-linked when gamma irradiation is used for sterilization of the powder component of the final product. In addition, if the binding agent is used as a part of the liquid component, it is already solubilized and therefore produces a much more homogeneous bone cement when it is combined with the powder component. In addition, the amount of binding agent needed is reduced in a liquid form, requiring less liquid to be used in the formulation, and resulting in a cement with stronger mechanical strength.

It is also preferred that the binding agent of the present invention is water soluble.

Examples of the binding agent which can be used in the invention, without limitation, are polyvinylpyrrolidone, a copolymer of N-vinylpyrrolidone and vinylesters, a cellulose derivative, such as hydroxypropyl methyl cellulose, methyl cellulose, hydroxypropyl cellulose, carboxymethyl cellulose, gelatin, xanthan gum, scleroglucan (ACTIGUM), sodium alginate and/or a mixture thereof.

Furthermore, the particle size and/or amount of the binding agent can be adjusted to modify the injectability (or viscosity) of the cement formulation.

In accordance with the present invention, the particle size of the binding agent is between about 1 μm to about 2500 μm, preferably between about 1 μm to about 1000 μm, and more preferably between 10 μm to about 250 μm. This means that at least about 25%, preferably about 50%, more preferably about 75% of the binding agent, by weight, falls within these ranges based on sieving.

With respect to the amount of the binding agent, the binding agent may be present in an amount of between about 1% and about 15%, more preferably between about 1% and about 3% based on the total weight of the formulation.

In a preferred embodiment of the present invention, the binding agent of the present invention is supplied to an end user as a liquid component dissolved in a solvent. In such preferred embodiment, the binding agent may be present in an amount of between about 3% and about 15%, more preferably between about 7% and about 12% based on the total weight of the liquid component.

Calcium Phosphate Minerals

The at least one source of calcium phosphate useful in accordance with the present invention generally includes numerous calcium phosphate minerals already known in the art, such as those taught by Brown and Chow in U.S. Reissue Pat. Nos. 33,161 and 33,221, Chow and Takagi in U.S. Pat. Nos. 5,522,893, 5,542,973, 5,545,294, 5,525,148, 5,695,729 and 6,375,992 and by Constantz in U.S. Pat. Nos. 4,880,610 and 5,047,031, teachings of which are incorporated herein by reference.

For example, the source of at least one calcium phosphate mineral in accordance with the present invention includes tetra-calcium phosphate, di-calcium phosphate, tri-calcium phosphate, mono-calcium phosphate, β-tricalcium phosphate, α-tricalcium phosphate, oxyapatite, or hydroxyapatite and/or a mixture thereof.

In a preferred embodiment, two different calcium phosphate minerals are used in accordance with the present invention, more preferably one of two calcium phosphate minerals is tetra-calcium phosphate.

In another preferred embodiment, the at least one calcium phosphate mineral includes di-calcium phosphate and tetra-calcium phosphate, most preferably di-calcium phosphate dihydrate (also known as di-calcium phosphate dihydrous) ("DCPD") and tetra-calcium phosphate ("TTCP").

In yet another preferred embodiment, the at least one source of calcium phosphate mineral includes two calcium phosphate minerals, wherein one of the two calcium phosphate minerals is stabilized using a stabilizing agent.

A stabilizing agent is any material (with at least one calcium phosphate mineral) that will allow the calcium phosphate mineral to set when reacted after the calcium phosphate has been stored for a predetermined period of time, preferably for at least 5 months, more preferably for at least 3 months, and most preferably for at least 6 months or more according to the accelerated aging test described in details below.

For example, the source of the calcium phosphate mineral which can be used with a stabilizing agent in accordance with the present invention includes tetra-calcium phosphate, di-calcium phosphate, tri-calcium phosphate, mono-calcium phosphate, β-tricalcium phosphate, α-tricalcium phosphate, oxyapatite, or hydroxyapatite and/or a mixture thereof.

In a preferred embodiment, the stabilizing is added during the process of making the calcium phosphate mineral to make the stabilized calcium phosphate mineral.

The preferred source for making the stabilized calcium phosphate is di-calcium phosphate, more preferably DCPD.

Examples of the stabilizing agent which can be used in accordance with the present invention, without any limitation, are MgO, $MgO_2$, $Mg(OH)_2$, $MgHPO_4$, $MgHPO_4.3H_2O$, $MgHPO_4.7H_2O$, $Mg_3(PO_4)_2$, $Mg_3(PO_4)_2.4H_2O$, $Mg_3(PO_4)_2.8H_2O$, $Mg_3(PO_4)_2.22H_2O$, $MgCO_3$, $MgCO_3.3H_2O$, $MgCO_3.5H_2O$, $3MgCO_3Mg(OH)_2.3H_2O$, $MgCO_3Mg(OH)_2.3H_2O$, $Mg(C_3H_5O_3)_2.3H_2O$, $MgC_2O_4.2H_2O$, $Mg(C_4H_4O_6)_2.4H_2O$, $MgCO_3.CaCO_3$, $Mg_2P_2O_7$, $Mg(C_{12}H_{23}O_2)_2.2H_2O$, $Mg(C_{14}H_{27}O_2)_2$, $Mg(C_{18}H_{33}O_2)_2$, or $Mg(C_{18}H_{35}O_2)_2$ and/or a mixture thereof. The most preferred stabilizing agent is magnesium oxide.

In another preferred embodiment, a stabilizing agent is provided in an amount from about 10 ppm to about 60 ppm, preferably from about 30 ppm to about 50 ppm, more preferably about 40 ppm relative to the total weight of the calcium phosphate mineral to which the stabilizing agent is added to make the stabilized calcium phosphate mineral.

In a preferred embodiment when the at least one calcium phosphate includes DCPD and TTCP, a stabilizing agent, such s magnesium oxide is provided in an amount from about 10 ppm to about 60 ppm, preferably from about 30 ppm to about 50 ppm, more preferably about 40 ppm relative to the total weight of the DCPD.

Furthermore, the particle size of the at least one calcium phosphate can be adjusted to modify the rate of the rapid dissolution of calcium phosphate minerals during cement mixing and injection.

In accordance with the present invention, the particle size of the at least one calcium phosphate is between about 0.4 μm to about 200 μm, preferably between about 5 μm to about 175 μm, and most preferably between 25 μm to about 70 μm, as measured by Becton Coulter's LS 13 3220 series particle size analyzer as mentioned above, but using Isopropyl Alcohol (IPA) as the carrier medium. This means that at least about 25%, preferably about 50%, and more preferably about 75% of the at least one calcium phosphate, by weight, falls within these ranges based on sieving.

In a preferred embodiment wherein the at least one calcium phosphate includes DCPD and TTCP, the particle size of the DCPD is between about 0.4 μm to about 200 μm, preferably about 25 μm to about 70 μm, and most preferably about 40 μm to about 50 μm, and the particle size of TTCP is between about 0.4 μm to about 200 μm, preferably about 10 μm to about 30 μm.

In another preferred embodiment of the present invention, the at least one calcium phosphate of the present invention is supplied to an end user as a powder component. In such preferred embodiment, the at least one calcium phosphate may be present in an amount of between about 50% and about 90%, more preferably between about 60% and about 80% based on the total weight of the powder component.

In yet another preferred embodiment, wherein the at least one calcium phosphate mineral includes two calcium phosphate minerals, more preferably the stabilized DCPD and TTCP, the stabilized DCPD may be present in an amount of between about 15% and about 40%, more preferably between about 20% and about 30% based on the total weight of the powder component, and TTCP may be present in an amount of between about 45% and about 75%, more preferably between about 50% and about 70% based on the total weight of the powder component.

Sodium Phosphate Compound(s)

In accordance with the present invention, the at least one sodium phosphate compound is used to speed the setting time of the bone cement.

Examples of sodium phosphates which can be used in the present invention, without limitation, are disodium hydrogen phosphate anhydrous, sodium dihydrogen phosphate monohydrate, sodium phosphate monobasic monohydrate, sodium phosphate monobasic dihydrate, sodium phosphate dibasic dihydrate, trisodium phosphate dodecahydrate, dibasic sodium phosphate heptahydrate, pentasodium tripolyphosphate, sodium metaphosphate, and/or a mixture thereof.

In a preferred embodiment, the at least one sodium phosphate compound is two sodium phosphate compounds, more preferably disodium hydrogen phosphate anhydrous and sodium dihydrogen phosphate monohydrate.

The particle size of the at least one sodium phosphate compound is between about 1 μm to about 2500 μm, preferably between about 1 μm to about 1000 μm. This means that at least about 25%, preferably about 50% and more preferably about 75% of the sodium phosphate compound(s), by weight, falls within these ranges based on sieving.

In accordance with the present invention, the reaction retarding agent can be provided as a powder component, or dissolved in a solvent and provided as a liquid component.

The sodium phosphate compound may be present in an amount of between about 0.5% and about 5%, more preferably between about 0.5% and about 2.5%, based on the total weight of the total formulation.

In another preferred embodiment wherein the sodium phosphate compound is supplied to an end user as a liquid component, the sodium phosphate compound may be present in an amount of between about 1% and about 20%, more preferably between about 1% and about 10%, based on the total weight of the liquid component.

Solvent

Examples of solvent which can be used in accordance with the present invention includes, without limitation, water, blood, saline solution, PBS (phosphate buffered saline) and the like and the mixture thereof. The most preferred solvent is water.

The solvent may be present in an amount of between about 15% and about 30%, more preferably between about 18% and about 25%, based on the total weight of the total formulation.

In another preferred embodiment, the solvent may be present in an amount of between about 50% and about 95%, more preferably between about 75% and about 90%, based on the total weight of the liquid component.

Additive(s)

Various additives may be included in the inventive cements, slurries and pastes to adjust their properties and the properties of the hydroxyapatite products made from them. For example, proteins, osteoinductive and/or osteoconductive materials, X-ray opacifying agents, medicaments, supporting or strengthening filler materials, crystal growth adjusters, viscosity modifiers, pore forming agents, and other additives and a mixture thereof may be incorporated without departing from the scope of this invention.

The inventive cement may be supplied to the user in a variety of forms, including as powders or as powder mixture which is later mixed with a solvent to make slurry or putty; or as a pre-mixed putty which may contain a nonaqueous extender, e.g., glycerine and/or propylene glycol.

It may be supplied with or in the instrumentation which is used to introduce the cement into the body, for example, a syringe, percutaneous device, cannula, biocompatible packet, dentula, reamer, file or other forms which will be apparent to those of ordinary skill in the art.

It is contemplated that the cement in any of these forms, may be made available to the surgeon, veterinarian or dentist via a kit containing one or more of its key components.

The cement is generally provided or employed in a sterilized condition. Sterilization may be accomplished, by e.g., radiation sterilization (such as gamma-ray radiation), moist heat sterilization, dry heat sterilization, chemical cold sterilization, and filtration.

Moreover, as will be recognized by those of skill in the art, numerous other specific techniques for preparation of each component (e.g. at least one calcium phosphate mineral, preferably the stabilized calcium phosphate mineral, at least one reaction retarding agent, and at least one binding agent and etc.) of the inventive cement may be employed.

For example, the conventional precipitation and crystallization methods can be used in preparation of the calcium phosphate minerals. Drying of the precipitates and/or crystals can be accomplished using the conventional drying methods such as freeze drying, oven drying, vacuum drying and the like.

Furthermore, each component described in accordance with the present invention herein (such as at least one reaction retarding agent, at least one binding agent, solvents and additives and etc.) may also be purchased if there is a commercially available product.

Similarly, the particle size reduction of these elements can be accomplished by using, for example, a pestle and mortal, a ball mill, a roller mill, certifugal-impact mill and sieve, cutter mill, attrition mill, chaser mill, fluid-energy mill and/or centrifugal-impact pulverizer.

This invention is illustrated by, but not limited to, the following examples. Although the following Examples may recite a certain order of steps of making the invention, the invention is not in anyway limited to the order written.

EXAMPLE 1

Production of DCPD with 40 ppm of Magnesium (1) 30% Phosphoric Acid Solution Preparation With 40 ppm Magnesium Addition To make the required 30% concentration of orthophosphoric acid ($H_3PO_4$), in a 5 ltr stainless beaker, 261+/−2 mls of 85% orthophosphoric acid was added to 737+/−2 mls of deionized water and the beaker was placed on top of a hot plate set to 45° C. Then the temperature probe was placed in the beaker to measure the temperature of the acid solution and the hot plate was turned on to heat the solution to 45° C. The solution was then stirred at a speed of 200+/−10 rpm to ensure that the probe was measuring a true representation of the beaker content. While the acid solution was being heated to 45° C., 0.0413 grams of magnesium oxide (MgO) (equivalent to about 40 ppm magnesium content or about 0.006883% based on the weight of the DCPD) was added to the solution, which is herein also referred to as magnesium "spiked" solution or magnesium "spiked" orthophosphoric acid. Then the pH probes and temperature probes were calibrated and put into the acid solution.

(2) Preparation of Calcium Carbonate Solution 0.45 kg of calcium carbonate ($CaCO_3$) was added into a 5 kg stainless steel beaker and 1 ltr of deionized water was added to the beaker. The beaker was then placed on top of a hot plate which was set to 40° C. Then the temperature probe was placed into the calcium carbonate suspension and the hot plate was turned on. The calcium carbonate suspension was then stirred at a speed of 575+/−50 rpm to ensure that the probe was measuring a true representation of the beaker content.

(3) Wet Chemical Precipitation

Once the magnesium spiked orthophosphoric acid reached the temperature of 45° C. and calcium carbonate suspension reached the temperature of 40° C., Watson-Marlow's Model 323u/D peristaltic pump system was set up to feed the carbonate suspension into the magnesium spiked orthophosphoric acid at a feed rate of 48+/−2 ml/min. The pH probe was activated in order to obtain the temperature/pH/time data at the start. Then the carbonate suspension was fed into the acid solution. Once the pH of the acid solution reached a pH of ~3.6, the feed rate of the carbonate suspension was stopped and the pH of the solution was monitored. The pH data from the beginning till the end of the carbonate feed was recorded. Once the pH reached 4.75, the final temperature/pH/time data for the precipitate was recorded and all the temperature and pH probes as well as the peristaltic tube from the solution were removed. The reaction of magnesium, orthophosphoric acid and calcium carbonate produced the stabilized DCPD precipitate.

(4) Precipitate Rinsing

A Whatman #5 filter paper (2.5 μm pore size) was placed into each Buckner funnel attached to a Buckner flask. Five (5) Buckner funnels attached to Buckner flasks were needed per precipitation run. Then, the precipitate solution (approximately 300 ml) was poured into each Buckner funnel attached to a Buckner flask and then a vacuum pump was turned on. The pump drew a vacuum and caused the water to be removed from the precipitate while the filter paper kept the precipitate in the Buckner funnel. After a minimum of two minutes of suction, each Buckner funnel was filled to the rim with deionized water (approx. 200-300 ml) in order to rinse any excess reactants from the precipitate. The precipitate was left under the vacuum for a minimum time of 5 minutes in order to ensure removal of any excessive free moisture.

(5) Freeze Drying

Next, a maximum of 300 grams (approximately half a precipitate production yield) was placed per freeze-drying tray in a manner ensuring that the precipitate is spread out evenly on the tray. The filled trays were then placed into Biopharma Process System's Model VirTis Genesis 25 Super ES freeze dryer. Each tray contained a temperature probe in order to monitor the precipitate temperature/moisture level during drying. Then the freeze dryer cycle was set to the program listed below and was turned on.

TABLE 1

Freeze Drying Recipe for DCPD

| Step | Temperature (° C.) | Time (minutes) | Vacuum (mTorr) |
|---|---|---|---|
| *R | −15 | 1 | 100 |
| **H | −15 | 120 | 100 |
| R | −5 | 120 | 200 |
| H | −5 | 240 | 200 |
| R | 0 | 120 | 1000 |
| H | 0 | 600 | 1000 |
| R | 10 | 60 | 1000 |
| H | 10 | 30 | 1000 |
| R | 20 | 60 | 1000 |
| H | 20 | 30 | 1000 |

*R = Ramp section of the freeze drying cycle.
**H = Hold section of the freeze drying cycle.

Once the precipitate has been dried using the freeze-drying cycle listed in Table 1, the precipitate required milling in order to reduce the average particle size so as to improve the final cement handling and setting properties. This milling is performed using Glen Creston Ltd's Model BM-6 roller ball-mill.

(6) Ball-Milling

3000+/−30 grams of alumina milling media (13.0 mm diameter×13.2 mm height) was placed into each ball-mill jar. Then, 500+/−25 grams of the dried DCPD precipitates were added into each ball-mill jar and were placed on the ball-mill rollers. The ball-mill was set to 170 rpm and a mill time of 30 minutes, and was turned on.

The ball-mill jar speed was monitored to ensure that it is rotating at 85 rpm. Once the 30 minutes of milling has elapsed, the milling media was separated from the milled powder by sieving through the 8 mm screen provided.

The milled and sieved powders were then placed into the freeze-drying trays and the freeze-drying procedure as detailed in the previous section was repeated.

As will be recognized by those of skill in the art, other specific techniques for preparation of the stabilized di-calcium phosphate component of the inventive cement may be employed.

For example, one may also use the following freeze drying and ball milling parameters in preparation of stabilized DCPD with 40 ppm of magnesium.

(7) Freeze Drying

A maximum of 500 grams was placed per freeze-drying tray in a manner ensuring that the precipitate is spread out evenly on the tray. The filled trays were then placed into Biopharma Process System's Model VirTis Genesis 25 Super ES freeze dryer. Each tray contained a temperature probe in order to monitor the precipitate temperature/moisture level during drying. Then the freeze dryer cycle was set to one of the following preferred programs listed below and was turned on.

TABLE 2

$1^{st}$ Freeze Drying Parameters for DCPD

| Step | Temperature (° C.) | Time (minutes) | Vacuum (mTorr) |
|---|---|---|---|
| *R | −5 | 1 | 100 |
| **H | −5 | 480 | 100 |
| R | 0 | 120 | 1000 |
| H | 0 | 600 | 1000 |
| R | 10 | 60 | 1000 |
| H | 10 | 90 | 1000 |
| R | 25 | 60 | 1000 |
| H | 25 | 90 | 1000 |

*R = Ramp section of the freeze drying cycle.
**H = Hold section of the freeze drying cycle.

Once the precipitate has been dried using the freeze-drying cycle listed in Table 1, the precipitate required milling in order to reduce the average particle size so as to improve the final cement handling and setting properties. This milling is performed using Glen Creston Ltd's Model BM-6 roller ball-mill.

(8) Ball-Milling

3000+/−25 grams of alumina milling media (13.0 mm diameter×13.2 mm height) was placed into each ball-mill jar. Then, 560+/−10 grams of the dried DCPD precipitates were added into each ball-mill jar and were placed on the ball-mill rollers. The ball-mill was set to 170 rpm and a mill time of 25+/−2 minutes, and was turned on.

The ball-mill jar speed was monitored to ensure that it is rotating at 87+/−5 rpm. Once the 25+/−2 minutes of milling has elapsed, the milling media was separated from the milled powder by sieving through the 8 mm screen provided.

The particle size of the powder components (including DCPD and TTCP) were measured using the above mentioned Beckman Coulter's LS 13320 Series particle size analyzer.

The milled and sieved powders (maximum weight of 375 g) were then placed into the freeze-drying trays and the freeze-drying procedure as detailed in Table 3 below.

TABLE 3

$2^{nd}$ Freeze Drying Parameters for DCPD

| Step | Temperature (° C.) | Time (minutes) | Vacuum (mTorr) |
|---|---|---|---|
| *R | −5 | 1 | 200 |
| **H | −5 | 60 | 200 |
| R | 0 | 60 | 1000 |
| H | 0 | 120 | 1000 |
| R | 10 | 60 | 1000 |
| H | 10 | 30 | 1000 |
| R | 20 | 60 | 1000 |
| H | 20 | 60 | 1000 |
| R | 30 | 60 | 1000 |
| H | 30 | 300 | 1000 |

*R = Ramp section of the freeze drying cycle.
**H = Hold section of the freeze drying cycle.

EXAMPLE 2

Production of DCPD with 60 ppm of Magnesium (1) 30% Phosphoric Acid Solution Preparation with 60 ppm Magnesium Addition To make the required 30% concentration of orthophosphoric acid ($H_3PO_4$), in a 5 ltr stainless beaker, 261+/−2 mls of 85% orthophosphoric acid was added to 737+/−2 mls of deionized water and the beaker was placed on top of a hot plate set to 47° C. Then the temperature probe was placed in the beaker to measure the temperature of the acid solution and the hot plate was turned on to heat the solution to 47° C. The solution was then stirred at a speed of 200+/−10 rpm to ensure that the probe was measuring a true representation of the beaker content. While the acid solution was being heated to 47° C., 0.0620 grams of magnesium oxide (MgO) (equivalent to about 60 ppm magnesium content or about 0.0085% based on the weight of the DCPD) was added to the solution. Then the pH probes and temperature probes were calibrated and put in to the acid solution.

(2) Preparation of Calcium Carbonate Solution 0.45 kg of calcium carbonate ($CaCO_3$) was added into a 5 kg stainless steel beaker and 1 ltr of deionized water was added to the beaker. The beaker was then placed on top of a hot plate which was set to 42° C. Then the temperature probe was placed into the calcium carbonate suspension and the hot plate was turned on. The calcium carbonate suspension was then stirred at a speed of 575+/−50 rpm to ensure that the probe was measuring a true representation of the beaker content.

(3) Wet Chemical Precipitation

Once the magnesium spiked orthophosphoric acid reached the temperature of 47° C. and calcium carbonate suspension reached the temperature of 42° C., Watson-Marlow's Model 323u/D peristaltic system was set up to feed the carbonate suspension into the magnesium spiked orthophosphoric acid at a feed rate of 48+/−2 ml/min. Then the pH probe was activated in order to obtain the temperature/pH/time data at the start. Then the carbonate suspension was fed into the acid solution. Once the pH of the acid solution reached a pH of ~3.6, the feed rate of the carbonate was stopped and the pH of the solution was monitored. The pH data from the beginning till the end of the carbonate feed was recorded. Once the pH reached 5.00, the final temperature/pH/time data for the precipitate was taken and all the temperature and pH probes as well as the peristaltic tube from the solution were removed. The reaction of magnesium, orthophosphoric acid and calcium carbonate produced the stabilized DCPD precipitate.

(4) Precipitate Rinsing

A Whatman #5 filter paper (2.5 µm pore size) was placed into each Buckner funnel attached to a Buckner flask. Five (5) Buckner funnels attached to Buckner flasks were needed per precipitation run. Then, the precipitate solution (approximately 300 ml) was poured into each Buckner funnel attached to a Buckner flask and then a vacuum pump was turned on. The pump drew a vacuum and caused the water to be removed from the precipitate while the filter paper kept the precipitate in the Buckner funnel. After a minimum of two minutes of suction, each Buckner funnel was filled to the rim with deionized water (approx. 200-300 ml) in order to rinse any excess reactants from the precipitate. The precipitate was left under the vacuum for a minimum time of 5 minutes in order to ensure removal of any excessive free moisture.

(5) Freeze Drying

A maximum of 300 grams (approximately half a precipitate production yield) was placed per freeze-drying tray in a manner ensuring that the precipitate is spread out evenly on the tray. The filled trays were then placed into Biopharma Process System's Model VirTis Genesis 25 Super ES freeze dryer. Each tray contained a temperature probe in order to monitor the precipitate temperature/moisture level during drying. Then the freeze dryer cycle was set to the program listed below and was turned on.

TABLE 4

Freeze Drying Parameters for DCPD

| Step | Temperature (° C.) | Time (minutes) | Vacuum (mTorr) |
|---|---|---|---|
| *R | −15 | 1 | 100 |
| **H | −15 | 120 | 100 |
| R | −5 | 120 | 200 |
| H | −5 | 240 | 200 |
| R | 0 | 120 | 1000 |
| H | 0 | 600 | 1000 |
| R | 10 | 60 | 1000 |
| H | 10 | 30 | 1000 |
| R | 20 | 60 | 1000 |
| H | 20 | 30 | 1000 |

*R = Ramp section of the freeze drying cycle
**H = Hold section of the freeze drying cycle Once the precipitate has been dried using the freeze-drying cycle listed in Table 4, the precipitate required milling in order to reduce the average particle size so as to improve the final cement handling and setting properties. This milling is performed using Glen Creston's Model BM-6 roller ball-mill.

(6) Ball-Milling

3000+/−30 grams of alumina milling media (13.0 mm diameter×13.2 mm height) was placed into each ball-mill jar. Then, 500+/−25 grams of the dried DCPD precipitates were added into each ball-mill jar and were placed on the ball-mill rollers. The ball-mill was set to 180 rpm and a mill time of 32 minutes, and was turned on.

The ball-mill jar speed was monitored to ensure that it is rotating at 95 rpm. Once the 32 minutes of milling has elapsed, the milling media was separated from the milled powder by sieving through the 8 mm screen provided. The milled and sieved powders have a particle size within generally a range of about 0.4 to about 200 µm, preferably about 35+/−20 µm, as measured by Beckman Coulter's Model LS 13320 Series particle size analyzer as explained above. The milled and sieved powders were then placed into the freeze-drying trays and the freeze-drying procedure as detailed in the previous section was repeated.

As will be recognized by those of skill in the art, other specific techniques for preparation of the stabilized di-calcium phosphate component of the inventive cement may be employed.

For example, one may also use the following freeze drying and ball milling parameters in preparation of stabilized DCPD with 60 ppm of magnesium.

(7) Freeze Drying

A maximum of 500 grams was placed per freeze-drying tray in a manner ensuring that the precipitate is spread out evenly on the tray. The filled trays were then placed into Biopharma Process System's Model VirTis Genesis 25 Super ES freeze dryer. Each tray contained a temperature probe in order to monitor the precipitate temperature/moisture level during drying. Then the freeze dryer cycle was set to the program listed below and was turned on.

TABLE 5

1$^{st}$ Freeze Drying Parameters for DCPD

| Step | Temperature (° C.) | Time (minutes) | Vacuum (mTorr) |
|---|---|---|---|
| *R | −5 | 1 | 100 |
| **H | −5 | 480 | 100 |
| R | 0 | 120 | 1000 |
| H | 0 | 600 | 1000 |
| R | 10 | 60 | 1000 |
| H | 10 | 90 | 1000 |
| R | 25 | 60 | 1000 |
| H | 25 | 90 | 1000 |

*R = Ramp section of the freeze drying cycle.
**H = Hold section of the freeze drying cycle.

Once the precipitate has been dried using the freeze-drying cycle listed in Table 5, the precipitate required milling in order to reduce the average particle size so as to improve the final cement handling and setting properties. This milling is performed using Glen Creston's Model BM-6 roller ball-mill.

(8) Ball-Milling

3000+/−25 grams of alumina milling media (13.0 mm diameter×13.2 mm height) was placed into each ball-mill jar. Then, 560+/−10 grams of the dried DCPD precipitates were added into each ball-mill jar and were placed on the ball-mill rollers. The ball-mill was set to 180 rpm and a mill time of 25+/−2 ppm, and was turned on.

The ball-mill jar speed was monitored to ensure that it is rotating at 87+/−5 rpm. Once the 25+/−2 minutes of milling has elapsed, the milling media was separated from the milled powder by sieving through the 8 mm screen provided. The milled and sieved powders have a particle size within generally a range of about 0.4 to about 200 µm, preferably about 47+/−22.5 µm, as measured by Beckman Coulter's Model LS 13320 Series particle size analyzer as explained above. The milled and sieved powders (maximum weight of 375 g) were then placed into the freeze-drying trays and the freeze-drying procedure as detailed in Table 6 below.

TABLE 6

2nd Freeze Drying Parameters for DCPD

| Step | Temperature (° C.) | Time (minutes) | Vacuum (mTorr) |
|---|---|---|---|
| *R | −5 | 1 | 200 |
| **H | −5 | 60 | 200 |
| R | 0 | 60 | 1000 |
| H | 0 | 120 | 1000 |
| R | 10 | 60 | 1000 |
| H | 10 | 30 | 1000 |
| R | 20 | 60 | 1000 |
| H | 20 | 60 | 1000 |
| R | 30 | 60 | 1000 |
| H | 30 | 300 | 1000 |

*R = Ramp section of the freeze drying cycle.
**H = Hold section of the freeze drying cycle.

EXAMPLE 3

Production of Tetra Calcium Phosphate (TTCP)

(1) TTCP Cake Preparation

To form the preferred TTCP, the TTCP slurry mixture needs to comprise a 50% w/w solution of solid to liquid with the solid component comprising 60.15% di-calcium phosphate anhydrous (DCPA) and 39.85% $CaCO_3$ and the liquid component comprising purified water. To prepare a batch of TTCP "cakes" for sintering in the furnace, i.e., 3500 grams of TTCP cakes, 2105.25+/−0.5 grams of DCPA was accurately weighed out into a clean 5 liter Buckner flask. To this, 1394.75+/−0.5 grams of $CaCO_3$ were added. To this powder mixture, 3.5 liters of deionized water was added. Table 7 shows the specific amounts and percentages of these components.

TABLE 7

Raw Material Weights for the Production of TTCP Cakes

| Material | Weight (g) | Ratio (%) |
|---|---|---|
| $CaCO_3$ | 1394.75 ± 1 | 39.85 |
| DCPA | 2105.25 ± 1 | 60.15 |
| Water | 3500.00 ± 10 | 100 |

The Buckner flask was then sealed with appropriate rubber bung and nozzle attachments. The Buckner flask was placed in Glen Creston Ltd's Model T10-B turbular mixer for 20 minutes for homogenous mixing. Table 8 shows the turbular blending parameters.

TABLE 8

Turbular Parameters for Blending of TTCP Raw Materials

| Parameter | Setting |
|---|---|
| Speed (rpm) | 44 ± 4 |
| Time (mins) | 20 |
| Buckner Flask Volume (%) | 80 |

While the Buckner flask was mixing, the appropriate vacuum tubing to a four-point manifold was connected: one end was attached to the vacuum pump, the other four points were attached to the nozzle attachments on four Buckner flasks. A 9 cm diameter polypropylene Buckner funnel was assembled onto each of the four Buckner flasks, respectively, and Whatman grade 5 filter paper was placed into each Buckner funnel. The blended $DCPA/CaCO_3$/water mixture was removed from the turbular mixer, and the rubber bung was removed. Then, each polypropylene Buckner funnel was completely filled with the TTCP slurry. The TTCP slurry was vacuum dried using the vacuum pump, and the vacuum was drawn for a minimum of 5 minutes until the cakes formed solid top surfaces. Further vacuum drying could be used if required to form solid cakes. Once the cakes were formed, the vacuum on the Buckner flasks was released. Each funnel was removed from the flask and the inverted funnel was gently tapped to remove the cake. Each funnel produced a cake of approximately 300 grams.

Then the spent filter paper was removed, the funnel was washed out with purified water and a fresh filter paper was placed in the funnel. The above steps were repeated until all the slurry solution is in a cake form. The TTCP slurry was hand mixed every four to five cake preparations to ensure homogeneity. If upon removal from the funnel, the cake was broken or has a rough surface, the deionized water was sprayed onto the surface to bind loose fragments together. Any loose remaining fragments were reintroduced to the slurry mixture to form new cakes.

(2) Sintering

All cakes were stacked onto a stainless steel tray and dried for two hours at 200° C. in Lenton's Model AWF 12/42 muffle furnace to drive off excess moisture prior to sintering. The TTCP cakes were now ready to be sintered using the sintering program detailed in Table 9.

TABLE 9

Sintering Parameters for Firing of TTCP Cakes

| Step | Temperature (° C.) | Time (minutes) | Ramp Rate (° C./min) |
|---|---|---|---|
| Ramp | 800 | 100 | 8 |
| Dwell | 800 | ≧120 | n/a |
| Ramp | 1550 | 94 | 8 |
| Dwell | 1550 | 720 | n/a |
| Cool | 800 | ≦10 | 75 |
| Cool | 20 | 15 | 52 |

The sintered cakes were transferred to a vacuum Buckner flask before the temperature dropped below 150° C. unless the material was to be crushed and milled immediately.

(3) Jaw Crushing

TTCP was processed through Glen Creston's jaw crusher to reduce the granules to a manageable size, preferably in the range of about 2.5 to about 7.5 mm prior to processing through the co-mill. The sintered TTCP cakes were manually broken using a mortar and pestle to particle sizes of approximately one inch in diameter before loading into the jaw crusher. In this instance, the jaw crusher gap was set to 5 mm.

(4) Co-Milling of TTCP Granules

TTCP was processed through Quadro Inc.'s co-mill (Model Quadro Comil 197) to reduce the material to the final particle size. The mill speed was set to 5000+/−300 rpm. The impeller gap was set to 0.375" using stainless steel washers. To co-mill the TTCP powder, the jaw-crushed TTCP powders were slowly fed into the co-mill at a rate of approximately 700 grams/min, ensuring that the co-mill did not become clogged with excess powder. (See Table 10 for co-milling parameters.)

TABLE 10

Parameters for Co-Milling the Jaw-Crushed Sintered TTCP Cakes

| Parameter | Setting |
|---|---|
| Screen No. | 0.024" |
| Impeller speed | 5000 rpm |

(5) Ball-Milling

Glen Creston Ltd's Model BM-6 roller ball mill was used to ball-mill the sintered, jaw crushed and co-milled TTCP. The ball milling parameters for the dry milling of the sintered, jaw crushed and co-milled TTCP are listed in Table 6. For the dry milling of the TTCP, a total of 3000+/−25 grams of alumina milling media (13.0 mm diameter×13.2 mm height) was weighed into an alumina ball-milling jar, to which 600+/−25 grams of the TTCP was added. The ball mill parameters are outlined in Table 11 below.

TABLE 11

Milling Parameters for the Dry Ball-Milling of TTCP
TTCP Ball Mill Parameters

| Speed (rpm) | 87 +/− 5 |
|---|---|
| Time (mins) | 360 +/− 15 |
| Media fill weight (grams) | 3000 +/− 25 |
| TTCP weight (grams) | 600 +/− 25 |

The milled and sieved powders have a particle size within generally a range about 0.4 to about 200 μm, preferably about 10 to 30 μm. The particle size was measured as explained above using Beckton Coulter's LS 13 320 series particle size analyzer.

EXAMPLE 4

Preparation of a Reaction Retarding Agent (e.g. Trisodium Citrate)

Trisodium citrate (which was procured from ADM, Co. located in Cork, Ireland) was processed through Quadro Inc.'s co-mill (Model Quadro Comil 197) to reduce the material to the final particle size. The mill speed was set to 300+/−50 rpm. The screen size used was 0.039". The impeller gap was set to 0.05" using stainless steel washers. The trisodium citrate powder was slowly fed into the co-mill at a rate of approximately 700 grams/min, ensuring that the co-mill did not become clogged with excess powder.

EXAMPLE 5

Production of the Powder Component Containing DCPD, TTCP and Trisodium Citrate 28.6 weight % of stabilized DCPD with 60 ppm of magnesium, 61 weight % of tetra-calcium phosphate and 10.4 weight % of tri-sodium citrate were mixed to form a mixture.

TABLE 12

Powder Component of Bone Cement

| Chemical Name | Chemical Formula | Mw (grams) | % Weight/total weight of Powder Component |
|---|---|---|---|
| Stabilized DCPD with 40 ppm of Magnesium | $CaHPO_4 \cdot 2H_2O$ | 172.05 | 28.6 |
| Tetra-Calcium Phosphate | $Ca_4O(PO_4)_2$ | 366.26 | 61 |
| Tri-Sodium Citrate | $Na_3C_6H_5O_7 \cdot 2H_2O$ | 294.11 | 10.4 |
| TOTAL | | | 100 |

EXAMPLE 6

Production of Liquid Component Comprising Sodium Phosphates and Polyvinylpyrrolidone (PVP)

Into one liter of high purity water, 29.8 grams of disodium hydrogen phosphate anhydrous, 85.6 grams of sodium dihydrogen phosphate monohydrate and 90.0 grams of PVP were added and stirred until they were completely dissolved. All of the above-mentioned materials are readily available commercial products, and in this particular case, were procured following manufacturers.

The details of this preferred water-based solution are outlined in Table 13 below.

TABLE 13

Liquid Component of Bone Cement

| Chemical Name | Chemical Formula | Mw (grams) | % weight/total weight (weight (g)) |
|---|---|---|---|
| DiSodium Hydrogen Phosphate Anhydrous | $Na_2HPO_4$ | 141.96 | 2.5 |
| Sodium Dihydrogen Phosphate Monohydrate | $NaH_2PO_4 \cdot H_2O$ | 137.99 | 7.1 |
| Polyvinylpyrrolidone | $[-C_6H_9NO-]_n$ | $(111.1)_n$ | 7.5 |
| Water | $H_2O$ | 18 | 82.9 |

Below is another preferred embodiment of the liquid component of the present invention using sodium carboxymethylcelllose as a binding agent.

TABLE 14

Liquid Component of Bone Cement

| Chemical Name | Chemical Formula | Mw (grams) | Percentage % w/w |
|---|---|---|---|
| DiSodium Hydrogen Phosphate Anhydrous | $Na_2HPO_4$ | 141.96 | 2.7 |
| Sodium Dihydrogen Phosphate Monohydrate | $NaH_2PO_4 \cdot H_2O$ | 137.99 | 7.7 |
| Sodium carboxy-methylcellulose | $[-Na_2C_{16}H_{22}O_{14}-]_n$ | $(484.14)_n$ | 2.2 |
| Water | $H_2O$ | 18 | 87.4 |

EXAMPLE 8

Mixing of the Powder Component with the Liquid Component to Produce the Final Cement For the final cement usage, stabilized DCPD was mixed with the TTCP in an equimolar ratio (i.e. DCPD-to-TTCP ratio of 31.97:68.03). Then trisodium citrate was added to the mixture of DCPD and TTCP to produce a final ratio of DCPD:TTCP:sodium citrate of 28.6:61:10.4. This powder mixture was blended to ensure the formation of a mixture.

Then the liquid component was added to the powder mixture using a liquid-to-powder ratio of 0.32 to form a settable final product.

The bone cements of the present invention were subjected to an array of qualification tests to verify that they meet the performance requirements. The bone cements of the present invention were analyzed, for example, for their (1) long-term stability, (2) wet field penetration resistance, (3) compression strength, (4) mixing evaluation, (5) injectability, (6) percent washout, (7) hardware pull out, (8) hydroxyapatite conversion, and (9) shrinkage, which are described in more details below.

EXAMPLE 9

Test For Long-Term Stability

Figure 3:
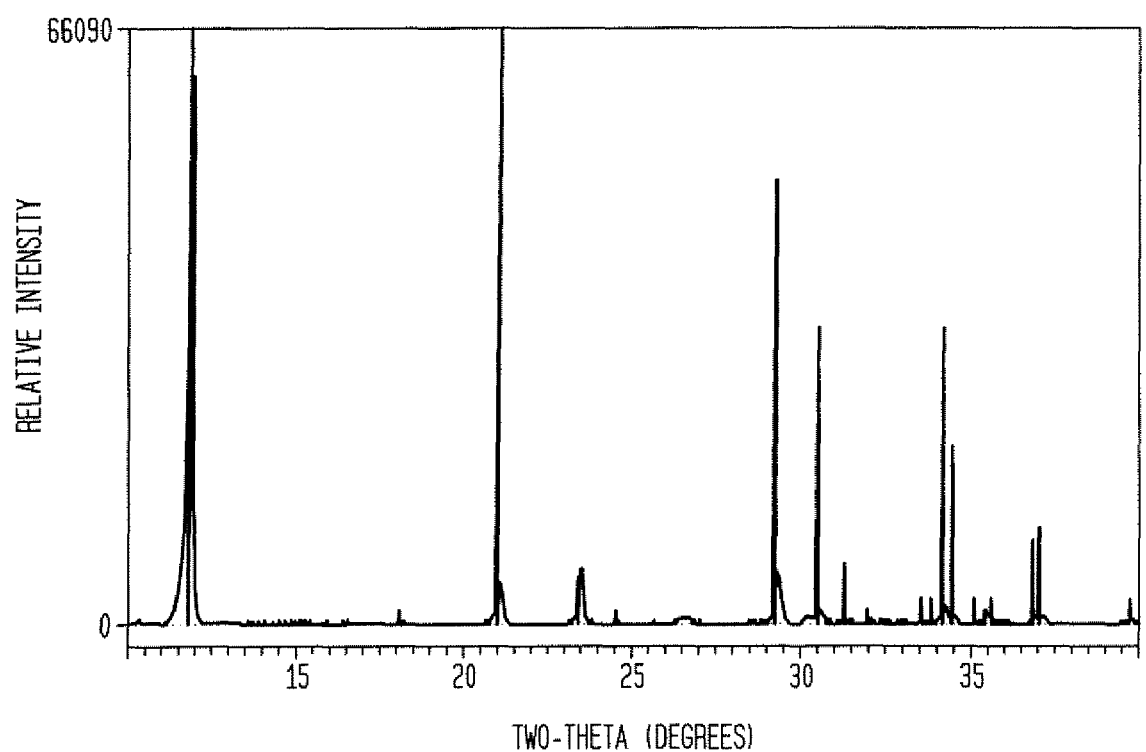
FIG. 3 is a characteristic X-ray powder diffraction pattern of DCPD containing 60 ppm of magnesium before the accelerated aging test.

The DCPD powders produced as described in Examples 1 and 2 were analyzed for long-term stability using an X-ray diffractometer. First, as shown in FIGS. 1 and 3, the X-ray powder diffraction patterns of the initial dry DCPD powders of Example 1 and Example 2 were collected using Rigaku's X-ray diffractometer.

Then, 5 grams of DCPD powders were packaged in a topaz bowl and heat-sealed with a breathable Tyvek lid. This bowl was then placed in a foil pouch with 10 grams of silicon desiccant. The foil pouch is then heat-sealed. The sealed foil pouch was then placed in a climatic oven set at 50° C. and aged for a set period of time. It has been determined that storage under these conditions for 52 days is equivalent to 1 year real time aging.

The stabilized DCPD powders were stored in a climatic oven set at 50° C. for 77 days, and the DCPD powders of Example 2 were stored in a climatic oven set at 50° C. for 91 days for accelerated aging tests.

Figure 2:
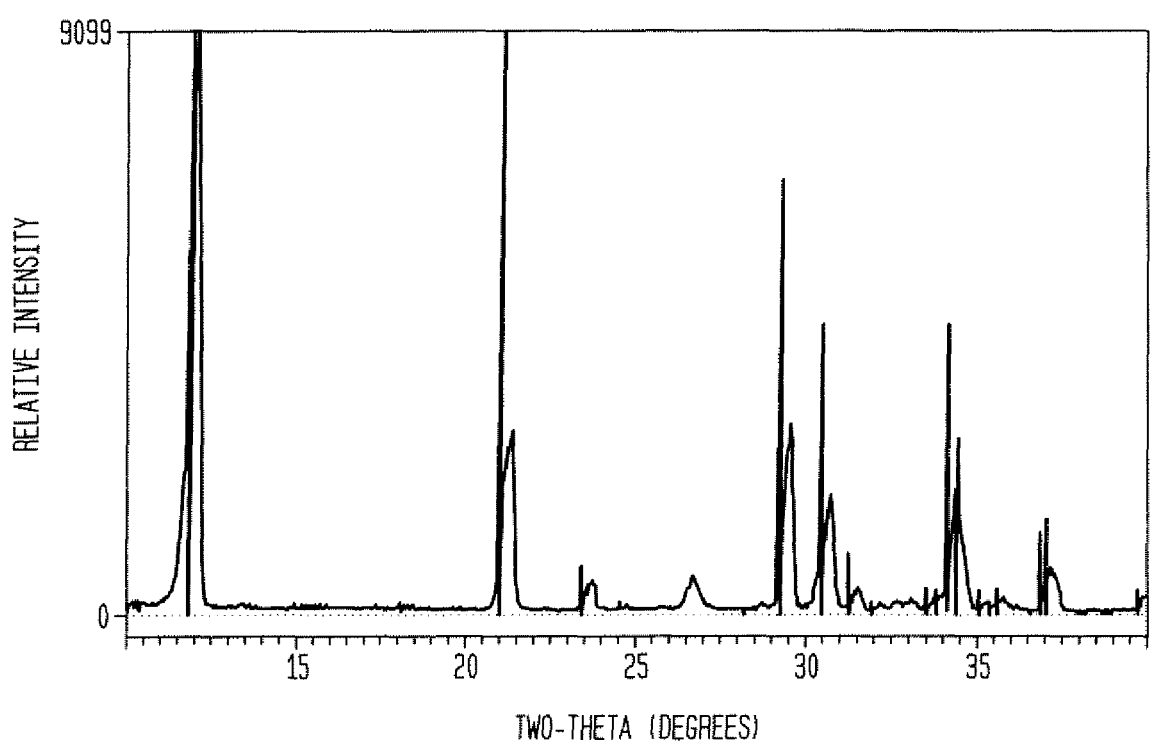
FIG. 2 is a characteristic X-ray powder diffraction pattern of DCPD containing 40 ppm of magnesium after the accelerated aging test (i.e., after storage at 50° C. for 77 days).
Figure 4:
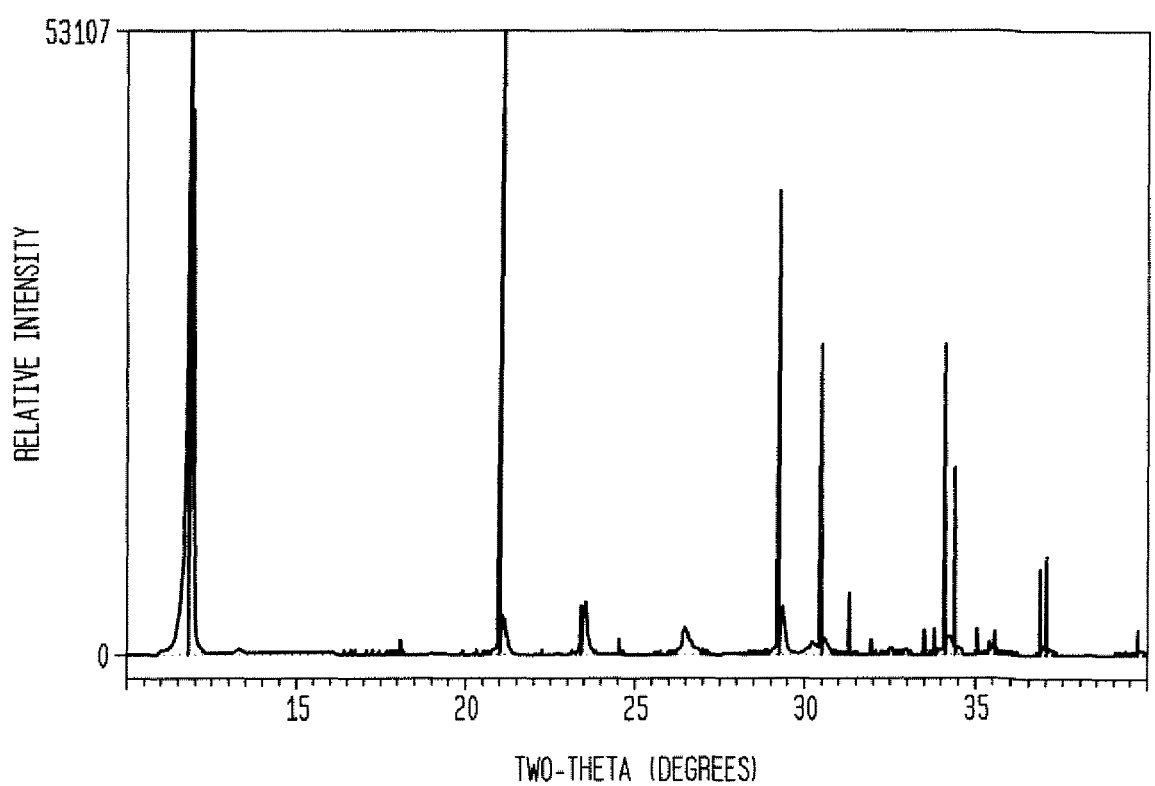
FIG. 4 is a characteristic X-ray powder diffraction pattern of DCPD containing 60 ppm of magnesium after the accelerated aging test (i.e., after storage at 50° C. for 90 days).

After the exposure in the accelerated aging test conditions, the X-ray powder diffraction patterns of the DCPD powders of Example 1 and Example 2 were collected again using the same Rigaku's X-ray diffractometer. As shown in FIGS. 2 and 4, said stabilized DCPD containing magnesium exhibited characteristic x-ray diffraction peaks of DCPD. More specifically, after the exposure in the accelerated aging test conditions as mentioned above, the X-ray powder diffraction patterns of the DCPD powders of Example 1 and Example 2, said stabilized DCPD powders exhibited x-ray diffraction peaks at 11.605, 20.787, 23.391, 26.5, 29.16, 30.484, 31.249, 31.936, 33.538, 34.062, 35.45, 36.34 and 39.67+/−0.2 degrees two-theta after an accelerated aging test of 52 days at 50° C. in a sealed container.

Similarly, a powder component of the final formulation (for example, a powder component comprising stabilized DCPD, TTCP or a powder component comprising stabilized DCPD, TTCP and a reaction retarding agent such as trisodium citrate) is also tested for long-term stability in the same fashion described above.

After the exposure in the accelerated aging test conditions for a predetermined period of time, the powder component can be tested for its stability by mixing it with a solvent to see whether it sets to form a cement. Alternatively, the powder component can be tested for stability using an x-ray diffractometer to determine whether the x-ray diffraction pattern exhibits the characteristic x-ray diffraction peaks of the original calcium phosphates of the powder component (such as DCPD and TTCP).

Based upon the Arrehnius equation as defined in ASTM F 1980, the following accelerated aging times equate to real time room temperature shelf-life:

| Real Time | Accelerated Time at 40° C. | Accelerated Time at 50° C. |
|---|---|---|
| 1.5 months | ~13 days | ~6.5 days |
| 3 month | ~26 days | ~13 days |
| 6 months | 53 days | 26 days |
| 1 year | 105 days | 52 days |
| 2 years | 210 days | 105 days |

EXAMPLE 10

Wet Field Penetration Resistance Test

The bone cements produced as described in Example 8 was also tested for wet field penetration resistance. The test consists of applying a load applicator through the cement at specific time points. The load applicator was made up of a small cylindrical stainless steel needle with 1/16" in diameter. Two minutes and thirty seconds after initial blending of the powder and liquid constituents, the cement was deposited into a long groove (¼" wide×¼" deep) of a block heated at 32° C. Three minutes after the initial blending, the cement was subjected to a constant flow of saturated phosphate solution using a Watson Marlow 323 peristaltic pump set at 20 rpm. The solution was kept constant at 32° C. Four minutes after the initial blending, the load applicator was made to penetrate the cement for 1.5 mm and the result force was recorded. The test is repeated every minute for 13 minutes. A stress/displacement curve was obtained at the end of the test to show the increase in resistance of the cement over time. The preferred penetration resistance requirements for the present invention were greater than 3500 psi (24.1 MPa) after 10 minutes from being mixed. Although the results below were measured after 10 minutes from the initial blending, the same test can be performed to determine whether the cement has set at 8 minutes or 9 minutes from the initial blending. Table 15 shows the results of the penetration resistance tests using the bone cements produced according to Example 8.

TABLE 15

| Penetration Resistance Test Results Bone Cement Containing DCPD with 40 ppm Of Magnesium (Example 1) | |
|---|---|
| Sample Number | Results |
| 1 | 4416 psi (30.45 MPa) @ 10 min |
| 2 | 4587 psi (31.63 MPa) @ 10 min |
| 3 | 4559 psi (31.44 MPa) @ 10 min |
| 4 | 4649 psi (32.06 MPa) @ 10 min |
| 5 | 4155 psi (28.65 MPa) @ 10 min |
| 6 | 4549 psi (31.37 MPa) @ 10 min |
| Sample Average | 4486 psi (30.93 MPa) @ 10 min |

EXAMPLE 11

Mixing Evaluation

Five random non experienced users of bone cements were presented with the powder and liquid components of the bone cement formulation of the present invention. The users were asked to mix and transfer a cement into the syringe fitted with a 10 gauge cannula at the ambient temperature of between 18° C. to 22° C. when they felt the mix was ready. The times taken for mixing and then transferring were measured from the initial blending of the powder and liquid components as recorded in the table below.

TABLE 16

| User | Mixing time | End of Transfer time |
|---|---|---|
| User 1 | 35 secs | 1 min 24 secs |
| User 2 | 54 secs | 1 min 53 secs |
| User 3 | 53 secs | 2 mins 5 secs |
| User 4 | 42 secs | 1 min 55 secs |
| User 5 | 45 secs | 1 min 52 secs |

The filled syringes were then taken to a test machine to carry out the injectability and wet field penetration tests, which are described in details below.

EXAMPLE 12

Injectability Test

As explained above in Example 11, the powder and liquid components were mixed to produce a cement paste and the paste was transferred to a syringe fitted with a 10 gauge cannula. Then, a downward force was applied on the plunger using a mechanical test machine with the speed set at 25 mm/min. A downward force was applied after 3 minutes and 30 seconds from initial blending of the powder and liquid components of the cement formulation. The readings were taken from the force/displacement curve at 25 mm displacement which is equivalent to 4 minutes and 30 seconds. For this test, maximum force at that time point is not to exceed 200N, preferably 150N. The results are recorded in the table below.

TABLE 17

| Test sample | Injection force at 3 mins 30 sec (N) |
|---|---|
| 1 | 73.1 |
| 2 | 73.3 |
| 3 | 77.3 |
| 4 | 111.6 |
| 5 | 67.2 |
| Average | 80.5 |

EXAMPLE 13

Wash Out Test

This test was performed in vivo during an animal study. Canine cranial defect was used as the site for evaluation of the washout. 5 cc of cement was implanted in the canine defect with the defect temperature of 32° C. and at 8 minutes, the cement was subjected to a pulse lavage from an Interpulse® squirt gun. The wash out was deemed to be acceptable as no significant amount of the cement was lost.

EXAMPLE 14

Hardware Pull Out Test

The cement was mixed and injected into an artificial cancellous bone material. Three minutes after the initial blending of the powder and liquid components, the artificial cancellous bone with injected bone cement (composite) was immersed into a phosphate solution, which was at 32° C. The composite was removed from the solution to be drilled in preparation for the screw at 9 minutes. At 10 minutes, the hardware (4.5 mm cortical screw) was screwed into the drilled composite and placed in the test rig ready for testing. At 12 minutes, the screw was pulled out of the composite using a mechanical test machine. The screw pull out force is to exceed 100N. The results are recorded in the table below.

TABLE 18

| Test sample | Pull out strength (N) |
|---|---|
| 1 | 156.2 |
| 2 | 193.4 |
| 3 | 530 |
| 4 | 554 |
| 5 | 500 |
| Average | 386.72 |

EXAMPLE 15

Hydroxyapatite Conversion

The cement was mixed and allowed to age for the appropriate time point in a phosphate solution at 37° C. At the specified time point, the cement was removed from the solution and dried in an oven at 70° C. The cement was then pulverized with the aid of a mortar and pestle and placed in a Rigaku x-ray diffractometer for XRD analysis. The sample was scanned between 10 and 40 degrees 2 theta and the results recorded on a graph of 2 theta versus intensity. The peaks for the sample were compared to JCPDS pattern 9-432 (for Hydroxyapatite) and the peak intensities at 2 theta of 29.23, 29.81, 31.77 and 32.20 were recorded for the calculation of HA conversion. The peaks at 2 theta of 29.23 and 29.81 correspond to TTCP and the peaks at 31.77 and 32.20 correspond to HA. The HA conversion was then calculated and the result at 2 weeks must be greater than 60% HA conversion. The results are recorded in the table below.

TABLE 19

| Test sample | HA conversion % (2 wks) |
|---|---|
| 1 | 61.3 |
| 2 | 76.7 |
| 3 | 62.7 |
| Average | 66.9 |

EXAMPLE 16

Shrinkage

The powder and liquid components were mixed and the paste was injected into a mold (21.3mm×6.1 mm). A total of three samples were prepared. The samples were allowed to set prior to removal from the mold. The volume was calculated from the diameter and height of each specimen. The samples were then incubated at 37° C. in a phosphate solution for 24 hours. They were subsequently removed and dried. Using a calibrated vernier, the specimens were measured again and the change in volume change calculated using the new measurements.

TABLE 20

| Test sample | Volume change % |
|---|---|
| 1 | 0.63 |
| 2 | 0.94 |
| 3 | 0.54 |
| Average | 0.70 |

As these and other variations and combinations of the features discussed above can be utilized without departing from the present invention as defined by the claims, the foregoing description of the preferred embodiments should be taken by way of illustration rather than by way of limitation of the invention as defined by the claims. It is therefore to be understood that numerous modifications may be made to the illustrative embodiments and that other arrangements may be devised without departing from the spirit and scope of the present invention as defined by the appended claims.

The invention claimed is:

1. A kit for forming a calcium phosphate bone cement comprising:
   (a) a first container comprising a premixed putty comprising stabilized di-calcium phosphate dihydrate containing from about 10 ppm to about 60 ppm of magnesium, at least one binding agent, and at least one sodium phosphate compound and
   (b) a second container comprising a premixed putty comprising a second calcium phosphate mineral, at least one reaction retarding agent, at least one binding agent, and at least one nonaqueous extender.

2. A kit for forming a calcium phosphate bone cement comprising:
   (a) a first container comprising a powder mixture of stabilized di-calcium phosphate dihydrate containing from about 10 ppm to about 60 ppm of magnesium, a second calcium phosphate mineral, and at least one reaction retarding agent, and
   (b) a second container comprising a solvent comprising at least one binding agent, and at least one sodium phosphate compound, wherein the first container is in close proximity with a desiccant.

3. The kit of claim 2, wherein said first container includes a moisture permeable barrier, and said first container and said desiccant are sealed in a substantially moisture impermeable package.

4. The kit of claim 2, wherein said desiccant is silicon.

5. The kit of claim 4, wherein the amount of silicon present is about 10 grams.

6. The kit of claim 2, wherein said desiccant is gamma-ray radiation compatible.

* * * * *